United States Patent [19]

Dunlap

[11] Patent Number: 5,062,830

[45] Date of Patent: Nov. 5, 1991

[54] DRY DISPOSABLE NOZZLE ASSEMBLY FOR MEDICAL JET INJECTOR

[75] Inventor: Kenneth W. Dunlap, Plymouth, Minn.

[73] Assignee: Derata Corporation, Minneapolis, Minn.

[21] Appl. No.: 503,948

[22] Filed: Apr. 4, 1990

[51] Int. Cl.$^5$ .............................................. A61M 5/30
[52] U.S. Cl. ......................................... 604/68; 604/72
[58] Field of Search ....................... 604/68, 69, 70, 71, 604/72, 275

[56] References Cited

U.S. PATENT DOCUMENTS

| | | |
|---|---|---|
| 2,754,818 | 7/1956 | Scherer . |
| 2,928,390 | 3/1960 | Venditty et al. ...................... 604/71 |
| 3,115,133 | 12/1963 | Morando . |
| 3,130,723 | 4/1964 | Venditty . |
| 3,189,029 | 6/1965 | Stephens . |
| 3,330,276 | 7/1967 | Gordon . |
| 3,688,765 | 9/1972 | Gasaway . |
| 3,908,651 | 9/1975 | Fudge . |
| 4,089,334 | 5/1978 | Schwebel . |
| 4,227,728 | 2/1988 | Dixon . |
| 4,507,113 | 3/1985 | Dunlap . |
| 4,518,385 | 11/1986 | Lindmayer . |
| 4,596,556 | 6/1986 | Morrow . |
| 4,623,332 | 3/1985 | Lindmayer . |
| 4,626,242 | 12/1986 | Fejes et al. ........................... 604/68 |
| 4,790,824 | 12/1988 | Morrow . |
| 4,874,367 | 10/1989 | Edwards . |

FOREIGN PATENT DOCUMENTS

| | | | |
|---|---|---|---|
| 1081193 | 5/1960 | Fed. Rep. of Germany ........ 604/70 |
| 863907 | 1/1958 | United Kingdom ................. 604/68 |

Primary Examiner—Stephen C. Pellegrino
Assistant Examiner—Glenn K. Dawson
Attorney, Agent, or Firm—Haugen and Nikolai

[57] ABSTRACT

A dry, disposable, low-cost nozzle assembly for a spring-powered medical injector power unit comprises a generally cylindrical molded plastic nozzle body which is removably attached to a medical injector module and it includes a longitudinal bore of a predetermined diameter and terminating in a conical segment short of the end surface thereof. A counterbore of a fine diameter is then formed between the apex and the end of the nozzle member, forming the ejector orifice. A seal member fits within the bore of the nozzle body and releasably attaches to the power unit's plunger. The seal member includes a conical tip dimensioned to fit with close tolerance in the conical segment of the body portion of the nozzle.

3 Claims, 2 Drawing Sheets

DRY DISPOSABLE NOZZLE ASSEMBLY FOR MEDICAL JET INJECTOR

BACKGROUND OF THE INVENTION

I. Field of the Invention

This invention relates generally liquid medicament, and more particularly to a single-use, low-cost, disposable nozzle assembly for a spring forward injector module.

II. Discussion of the Prior Art

Various forms of needleless hypodermic drug injection devices are known in the art. The Scherer U.S. Pat. No. 2,754,818 discloses one such device in which a disposable ampule filled with a predetermined dose of a wet medicine is loaded into a chamber proximate an ejection orifice in a permanent nozzle assembly. A powerful spring is cooperatively associated with a plunger and when the spring force is released, the plunger is driven to discharge the contents of the ampule through the orifice in a permanent nozzle.

The Gordon U.S. Pat. No. 3,330,276 describes another hypodermic jet injector device having the ability to draw a predetermined dosage of a liquid medicament from a supply vial, through a ball-valve arrangement into a cylinder containing a spring-loaded piston. When the spring energy is released, the piston is driven forward to force the liquid, under high pressure, out through the ejection orifice in a permanent nozzle.

The Dunlap U.S. Pat. No. 4,507,113, assigned to Derata Corporation of Minneapolis, Minn., (applicant's assignee), discloses a method and apparatus for filling the internal cylinder of a spring-powered jet injector from a supply vial directly through the ejection orifice, thereby obviating the need for a complex valve system. This results in essentially zero residual drug retention in the jet injection apparatus following the triggering thereof.

The above-identified patents each contemplates a device which includes a nozzle assembly forming a permanent part of the jet injector body. With the concern over the spread of AIDS, hepatitis and other viral diseases, medical practitioners have become quite concerned over the possibility of accidental "sticks" when drawing blood from a patient or when disposing of the conventional hypodermic needles in waste containers and the like. Thus, it is desirable to be able to administer drugs hypodermically, but without utilizing skin-penetrating needles.

The Lindmayer et al. U.S. Pat. No. 4,518,385 describes a needleless hypodermic injector incorporating a disposable syringe which comprises a tubular plastic barrel which includes an ejection orifice formed in a gem insert fitted into the tubular barrel. It further includes a plastic plunger slidably disposed in the barrel. Because the barrel is not designed to withstand the relatively high hydraulic pressures in encountered during the administration of a needleless injection, it is necessary in the Lindmayer design to provide a reusable head having the gem insert with the injection orifice embedded in the head. Because of the cost involved, the head is intended to be reusable for a series of injections and, thus, cannot be used in a clinic situation where drugs are to be administered to different patients. Moreover, in filling the barrel from a medicament vial, a needle is utilized to puncture the elastomeric seal on the vial cap. The current trend has been to eliminate needles of all types for the reasons already indicated.

In the case of the prior art needleless injectors heretofore described, during the administration of an injection, the fluid jet driven at high pressure through the patient's skin may result in some minor amount of bleeding and because the nozzle assembly of the jet injector is pressed firmly against the skin at the moment of release and for a short time thereafter, there is a possibility that blood might flow back into the ejection orifice to contaminate the nozzle. As such, to avoid cross-contamination of blood between different patient's being treated in a hospital or clinic situation, it would heretofore be necessary to disassemble the drug injector and sterilize those portions of the assembly that could conceivably retain contaminated blood.

SUMMARY OF THE INVENTION

In accordance with the present invention, all of the foregoing problems are obviated by providing a low-cost, disposable, single-use nozzle assembly for a medical drug injector, the disposable portion being sufficiently inexpensive so as to compete with conventional hypodermic needles. The nozzle assembly of the present invention comprises a simple two-piece molded assembly comprising a generally cylindrical nozzle unibody having a central longitudinal bore extending from a proximal end of the nozzle towards its distal end. The bore terminates in a conical segment whose apex is a short, predetermined distance proximal of the distal end of the nozzle unibody. A very small diameter counterbore is formed from the distal end to the apex of the conical segment, that counterbore comprising the ejection orifice.

The second piece of the two-piece nozzle assembly comprises a seal member having a conical head portion conforming to mate with the conical segment of the bore within the nozzle unibody along with integrally formed means for removably attaching that seal member to the plunger of the non-disposable drug injector power unit. That is to say, as the two-piece nozzle assembly is screwed onto or otherwise affixed to the end of the power unit, the seal member is simultaneously coupled to the power unit's plunger. A drug vial is then joined to the exterior of the nozzle assembly such that when the dosage control sleeve is rotated in the usual manner, the plunger and attached seal assembly will be drawn in the proximal direction creating a vacuum distally of the conical end of the seal member causing the liquid medicament to transfer from the supply vial into the chamber of the replaceable nozzle.

Once the correct dosage amount has been loaded into the nozzle chamber, the unit is ready to administer an injection. The ejection orifice in the nozzle is then placed against the patient's skin and a release button is depressed whereby the power spring delivers its force to a ram which is driven against the surface of the plunger, thus driving the seal with its conical tip to the end of the bore in the disposable nozzle unibody and ejecting the liquid medicament through the ejection orifice under very high pressure sufficient to penetrate the patient's skin.

Following the administration of injection, the nozzle assembly can be unscrewed or otherwise released from the end of the power unit and in doing so, the seal member is again released from the end of the plunger allowing the nozzle assembly to be thrown away. Because the nozzle assembly is free of sharp points, there can be no problem with accidental sticks during the handling and disposal of the medical waste. Because the seal member provides a barrier in the nozzle assembly, any minute amount of blood that may find its way back through the ejection orifice following the administration of an injection cannot cross that barrier to contaminate the non-disposable portion of the injector's power unit.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
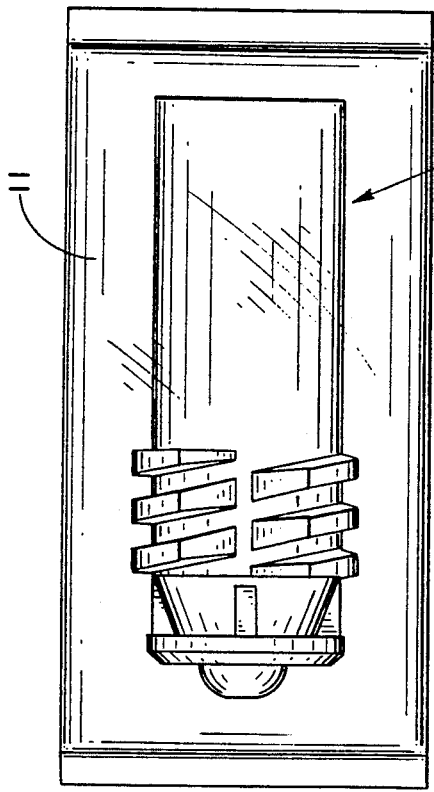
FIG. 1 illustrates the disposable nozzle assembly of the present invention contained in a sterile pack.
Figure 2:
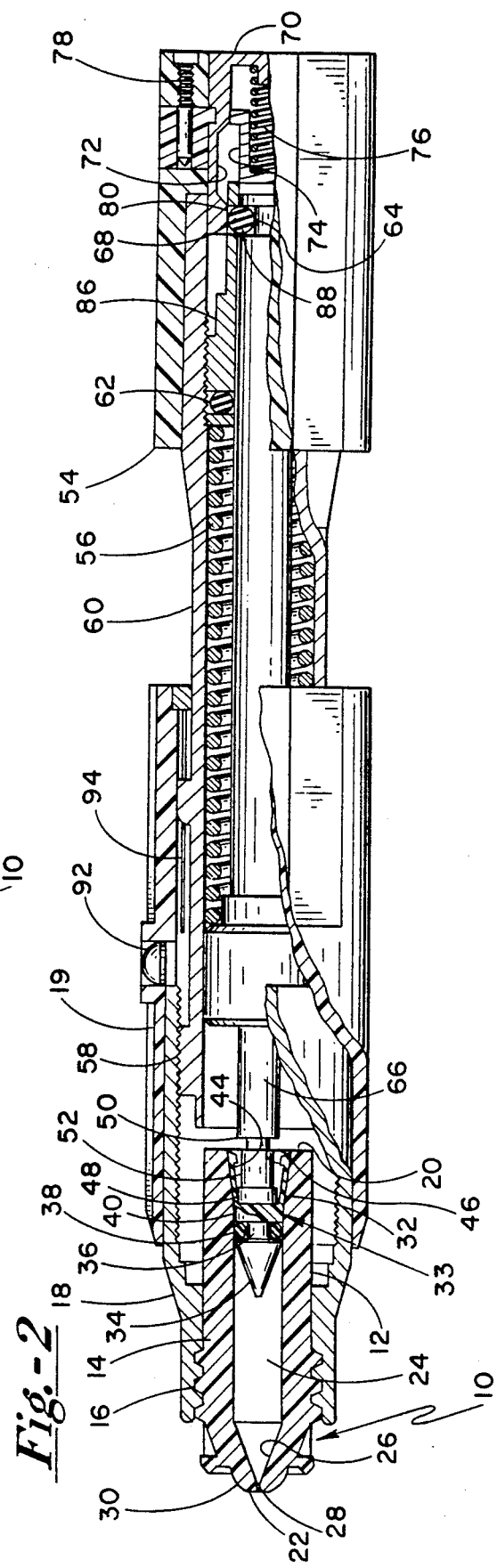
FIG. 2 is a cross-sectional view of the nozzle assembly including the disposable unibody and associated seal member affixed to the working end of a injector power unit.

Referring first to FIG. 1, there is shown a side elevation of the dry disposable nozzle assembly of the present invention indicated generally by numeral 10 contained in a sealed sterile package 12 in which it is stored prior to use. FIG. 2 shows a cross-sectional view of the assembly of FIG. 1 when attached to the working end of the medical injector power unit. As can be seen from these two figures, the replaceable, disposable nozzle assembly comprises a molded plastic nozzle body 14 of a generally cylindrical configuration and including coarse external threads 16 for mating with corresponding threads formed on the inner wall surface of the injector body 19. Rather than threads, the plastic body 14 may be coupled to the power unit with a bayonet coupling.

With no limitation intended, the nozzle member 14 may be fabricated from any one of a number of appropriate plastics but with a medical grade polycarbonate being preferred.

The molded plastic nozzle body 14 has a proximal end and a distal end 22. A centrally located longitudinal bore 24 extends from the proximal end 20 toward the distal end 22 and terminates in a contiguous conical segment 26 whose apex 28 is connected by a short counterbore 30 passing through the distal end 22 of the body. This counterbore 30 comprises the ejection orifice of the nozzle 10. A diameter of approximately 0.0065 inches for this counterbore has been found to be of a size suitable for providing a needleless injection of most liquid medicaments when used with a power spring driven plunger capable of developing 16000 PSI pressure.

It may further be noted from the cross-section of FIG. 2 that the bore 24 flares slightly near the proximal end 20. The function of this flared portion 32 will become apparent as the description continues.

With reference again to FIG. 1, packaged within the sterile envelope 11 and forming a part of the disposable nozzle assembly 10 is a seal member identified generally by numeral 33 in FIG. 2. The seal member comprises a conical nose portion 34 integrally formed with a cylindrical stem 36 which is surrounded by an elastomeric O-ring 38 dimensioned to form a liquid-tight sliding seal relative to the walls defining the bore 24. Integrally molded with the stem 36 is a cylindrical base portion 40 whose outside diameter also closely conforms to the diameter of the bore 24, preventing the elastomeric seal 38 from extruding into the interface between the cooperating members when subjected to operating pressures. The base portion 40 includes a plurality of tines as at 42 and 44 having barbed ends 46. The seal member 3 is preferably molded from Ultem ® high impact polycarbonate sold by the General Electric Company.

The dimensions of the conical tip portion 34 of the seal member 33 tapers at the same angle as the conical extension 26 of the longitudinal bore 24 and, as such, when the seal member 33 is driven in the distal direction in a manner to be later explained, any air or liquid which may be present in the bore 24 or its conical extension 26 will be driven out through the orifice 30.

Figure 3:
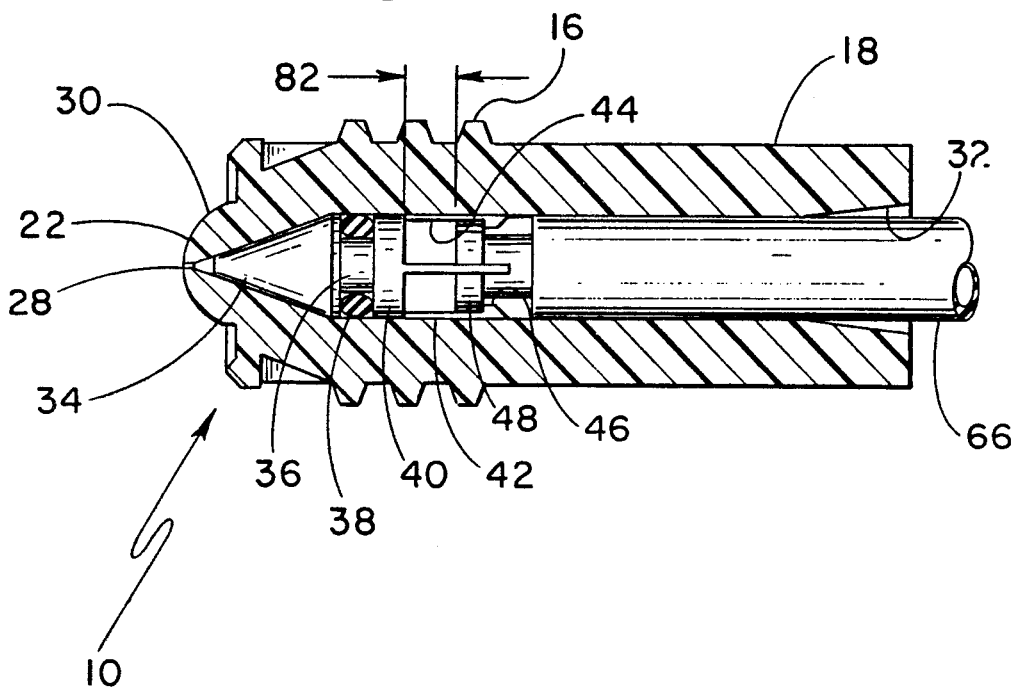
FIG. 3 is a cross-sectional view of the disposable nozzle assembly in accordance with the invention.

With reference to FIGS. 2 and 3, when the disposable assembly of FIG. 1 is screwed or otherwise secured to the working end of the power module, the head 48 of its plunger 50 fits between the tines or fingers when the seal member is positioned such that those tines reside in the flared portion 32 of the bore 24. When the plunger is advanced forward, i.e., in the distal direction, the tines 42 and 44 will flatten out upon reaching the end of the flared portion such that the barbs 46 thereon will fall into the grooved portion 52 of the injector's plunger 50, thus locking the seal member to the plunger.

The power unit portion of the medical injector is identified generally by numeral 54 and is shown partially in cut-away representation to reveal certain of its internal working parts. In that the invention resides primarily in the replaceable nozzle portion 10, it is not felt necessary to describe in great detail the construction of the power unit 54. It may, for example, comprise a Med II or a Med EZ type power pack available commercially from Derata Corporation of Minneapolis, Minn.

OPERATION

When the dry disposable molded plastic nozzle assembly of the present invention is fastened onto the power pack in the manner shown in FIG. 2, the winding sleeve 54 will first be turned clockwise with respect to the injector body 18 until a mechanical stop (not shown) is reached. The number of rotations will vary in accordance with the previous injection dosage. The clockwise rotation of the winding sleeve 54 functions to compress the power spring 56 through male and female threads 58 on the dosage sleeve 60 on injector body 18. The winding torque is resolved through thrust bearings 62 and the threads 58.

As the winding proceeds, the ball latch groove 64 in a latch rod 66 aligns with the latch ball's 68 in the groove 72 of the internal button 70. Further rearward travel of the ram simultaneously pushes the ball retainer 74 and the internal button 70 rearwardly. A ball retainer spring 76 assists the button to its most rearward stop position. At this point, the safety 78 may be pressed to engage and prevent accidental tripping of the device. The balls 68 are simultaneously driven into the ram groove 64 by the forward wedge angle of the button groove 72. The balls are thus trapped in the ram groove by the forward flat surface 80 of the button in the most rearward position. The button is mechanically stopped in the correct position by a stop surface on the safety latch 78. At the stop position, the ram will have over-traveled its ultimate latched position to assure that the balls are properly seated in the ram groove 64. During the winding sequence, the plunger assembly 50 forces the seal assembly 33 forward tightly into the conical segment 26 in the nozzle body 14. The free-travel impact gap 82 (FIG. 3) between the plunger 50 and the ram 66 will be zero at this time in the sequence.

With reference to the Dunlap U.S. Pat. No. 4,507,113, a vial containing a liquid medicament may be secured in the adapter described in that patent and then the adapter will be coupled to the nozzle portion of the injector such that the rounded nose on the nozzle is pressed against the diaphragm in the adapter, opening the zero clearance hole. Now, as the winding sleeve 54 is turned counterclockwise with respect to the injector body 18, the ram over-travel will be taken up and the rear wedge portion of the ram groove 72 will force the balls 68 outwardly against the forward flat surface 80 and against the forward surfaces of the latch housing 86.

The trigger mechanism is now latched with the spring fully compressed for maximum ejection power, and the safety 78 will be on. The plunger still rests at the bottom of its conical bore and the impact gap is still zero. As shown in FIG. 3, continued counterclockwise rotation of the sleeve 54 will move the plunger assembly 50 away from the ram and latch mechanism, developing the free travel impact gap 82 (FIG. 3) between the two assemblies. This free travel gap is preferably approximately 0.100 inches and is controlled by the linkage which couples the ram to the plunger assembly. This gap is developed due to seal friction between the O-ring 18 and the bore 24 as it is rotated away from the latched ram assembly 66. This rotation is accomplished on threads 58 which are mathematically calculated to correlate with the bore diameter and piston stroke to yield accurate dosage volume. At this point, a zero reading can be viewed through the dosage window 92. Further counterclockwise rotation of the winding sleeve 54 retracts the plunger and seal assembly in the nozzle 10 creating a vacuum in the bore or chamber 24–26 and drawing liquid relative to the travel of thread 58. The dosage is presented in the window 92 via a step-staggered decal 94.

With the device cocked and filled with medicament, an injection is administered by pressing the nose portion 22 of the nozzle against the skin of the patient. Upon releasing the safety 78 and depression of the button 70, the forward flat surface 80 of the button slides forward, allowing ball 68 to pop into the button groove 72 and simultaneously releases the ram 66 to move forward under the force of the power spring 56. The ball retainer 74 also moves forward with the ram. The retainer keeps the balls outward in the button groove 72 as the ram continues to move forward. The balls are contained laterally by guide holes 88 in the latch housing 86. The ram mass travels forward without restraint for the distance of the gap 82. Full penetration pressure of approximately 16,000 PSI is developed for a duration of approximately 300 microseconds with this impact force. The pressure then drops to about 1,800 PSI and then decreases at a rate proportional to the power spring rate for the balance of the injection duration which is dependent on dosage injected. This pressure is directly related to the effective hydraulic area of the seal assembly 32 and the spring rate of the power spring 56. The O-ring seal 38 on the assembly 33 is specifically designed to withstand the impulse penetrating pressure of 16,000 PSI and the associated wear at high pressures.

Following the administration of the injection, the nozzle assembly 10 can be unscrewed and pulled free of the power pack. As the nozzle assembly is pulled forward, the seal assembly 33 will be moved toward the proximal end 20 of the molded plastic nozzle 14 until the fingers or tines 44 and 46 spread apart into the taper 32. At this point, the plunger 52 can readily be removed from the seal 33.

ALTERNATIVE EMBODIMENT

Figure 4:
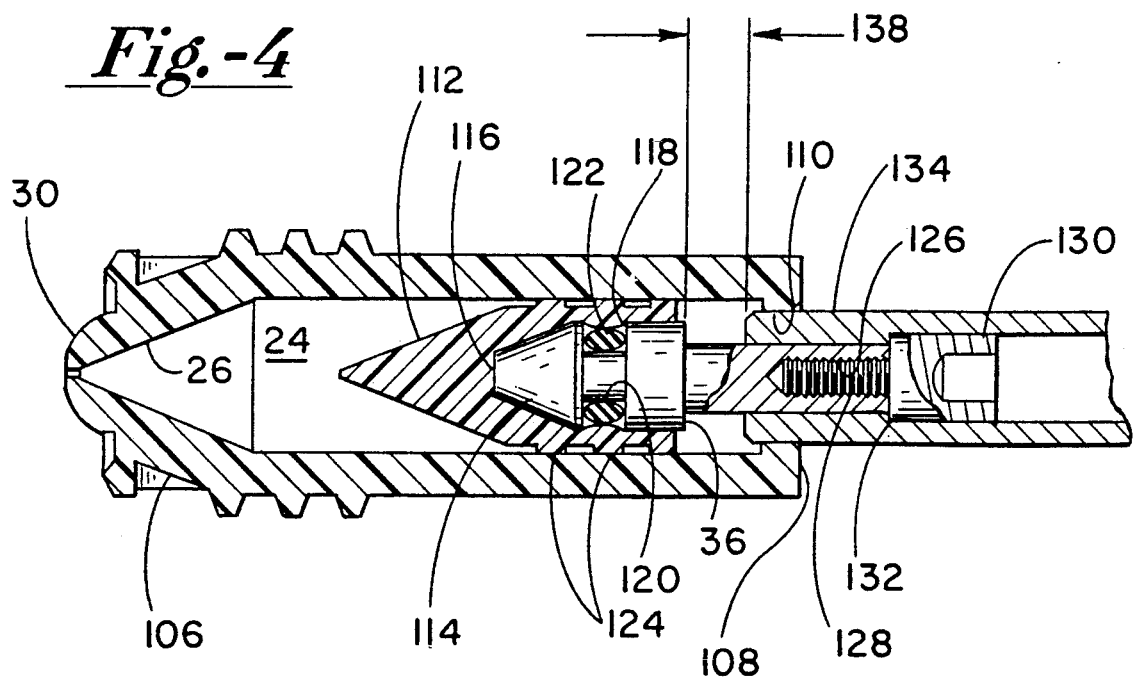
FIG. 4 depicts another embodiment of the invention illustrating an alternative way of coupling the seal member to the plunger.

Referring next to FIG. 4, there is shown a greatly enlarged side cross-sectional view of a dry disposable nozzle assembly in accordance with a further embodiment of the invention. Here, the molded plastic nozzle body 106 again includes the counterbore 28 forming the ejection orifice, a cylindrical bore 24 terminating in a right circular cone 26. The proximal end 108 of the molded plastic body includes an annular flange 110 of a predetermined diameter which is used to facilitate stripping the disposable seal member 112 free of the plunger body 114 which comprises a permanent part of the spring powered injector body.

In the embodiment of FIG. 4, the seal member includes a socket 116 shaped to generally conform to the outside contour of the plunger 114. The plunger itself includes an annular groove 118 for receiving an integrally formed annular ring 120 molded into the seal member 112. An O-ring spring 122 fits into the annular groove 118 in the plunger body 114 and applies an outward force to the seal member urging the annular sealing ribs 124 firmly against the cylindrical wall defining the bore 24.

The plunger 114 includes an internally threaded bore 126 coaxially aligned with the longitudinal axis of the assembly. This threaded bore cooperates with an externally threaded stud 128 formed on a free-travel adjust screw 130. This threaded adjust screw has a forward shoulder 132 cooperating with a corresponding shoulder formed in the ram 134. This permits a range of adjustment of ram-free travel before engaging the proximal edge 136 of the plunger 114. The free-travel gap is identified by numeral 138.

To understand the operation of the embodiment of FIG. 4, those skilled in the art will appreciate that the disposable seal member 112 is preassembled into the proximal end of the bore 24 in the molded plastic disposable nozzle body 106 and would normally be packaged in a sterile envelope to be used in providing a single injection. The Med-EZ ® manufactured and sold by Derata Corporation includes the permanently attached plunger assembly 114 with its O-ring spring 122. This plunger extends out of the distal end of the power pack and may be used to align the disposable nozzle assembly as it is screwed into the head of the power unit. When screwing the nozzle body in place, the plunger 114 enters the socket 116 formed in the seal 112 and locks into the socket to be held in place by the inner annular convoluted lip 120. When properly seated, the O-ring 122 provides an outwardly directed force to the walls of the seal to urge the annular sealing lips 124 against the inner wall of the cylindrical bore in the nozzle.

As the nozzle body is tightened onto the power pack, the preload spring force acts on the plunger to firmly seat the seal in the conical extension 26 of the bore. This purges all possible air which might be entrapped and thus assures accuracy of the dosage to be subsequently drawn. It has been found convenient to form a flat on the outer periphery of the O-ring to better distribute the sealing force over a wider area.

Prior to drawing liquid, the adapter and bottle of the Dunlap U.S. Pat. No. 4,507,113 is affixed to the exterior of the nozzle such that the rounded tip portion 22 thereof will distort the membrane to open the zero-clearance hole. Now, as the winding sleeve 54 (FIG. 2) is wound in the clockwise direction to begin the dosage draw sequence previously explained, the ram 134 will be drawn rearward to establish the penetration gap 138. The plunger remains stationary during this ram movement. As the head of free-travel adjust screw 128 engages the stop shoulder 132 in the ram 134, the plunger begins to move rearward, developing a vacuum in the bore 24-26. Because the seal 112 is now firmly engaged to the plunger 114, it moves rearward with the plunger. The volume of liquid drawn is determined by the amount of this linear travel and is displayed by a scale 92 on the power unit.

When the prescribed dosage is drawn, the adapter assembly and medicament vial is removed from the working end of the injection device and the head thereof is next pressed against the skin of the patient. When the button 70 (FIG. 2) is depressed, the spring force is released, driving the ram 134 against the plunger 114, forcing the conical end of the seal 112 up against the conical end portion 26 of the bore 24.

Next, following the administration of the injection, as the disposable nozzle assembly 10 is unscrewed to remove and discard it, the lip 110 on the molded plastic body functions to strip the seal 112 from the plunger 114, retaining the seal within the molded plastic disposable nozzle body so the two can be thrown away as a unit.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A dry disposable nozzle assembly for a hypodermic jet injector of the type including a body containing a power spring operatively coupled to a ram member which is movable at high velocity between a cocked position and a released position, said body further including a plunger assembly disposed within a generally tubular metal sleeve in the path of travel of said ram to be driven thereby where the plunger assembly includes a radial groove, said nozzle assembly including in combination:

(a) a disposable molded plastic nozzle of a generally cylindrical shape adapted to be disposed within and at least partly reinforced on the exterior thereof by said tubular metal sleeve and having first and second ends with an axial bore of circular cross-section extending from said first end toward said second end, said axial bore terminating in a generally conical segment having an apex lying on a longitudinal axis of said axial bore and a counterbore of a predetermined, small diameter relative to said axial bore extending from said second end to said apex and forming a one-piece ejection orifice;
   (b) means for removably attaching said molded plastic nozzle to said body within said metal sleeve; and
   (c) a disposable seal member encompassed by said molded plastic nozzle and fitted into said axial bore for longitudinal motion therein and including an integrally formed generally conical head dimensioned to fit within said generally conical segment of said axial bore with a predetermined close tolerance, said seal member including a socket formed in said seal member, said socket including a detent adapted to cooperate with said radial groove in said plunger assembly for receiving and releasably locking said plunger assembly.

2. The dry disposable nozzle assembly as in claim 1 wherein said seal member includes at least one annular, outwardly extending rib in wiping contact with the wall of said axial bore of circular cross-section.

3. The dry disposable nozzle assembly as in claim 1 wherein said ejection orifice of said nozzle has a diameter in the range of from 0.005 inch to about 0.007 inch.

* * * * *